(12) United States Patent
Kang et al.

(10) Patent No.: US 8,055,057 B2
(45) Date of Patent: Nov. 8, 2011

(54) METHOD FOR DETECTING DEFECTS IN A SUBSTRATE HAVING A SEMICONDUCTOR DEVICE THEREON

(75) Inventors: Moon-Shik Kang, Yongin-si (KR); Jong-An Kim, Seoul (KR); Myung-Sub Lee, Suwon-si (KR); Yu-Sin Yang, Seoul (KR); Ji-Hye Kim, Anyang-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 969 days.

(21) Appl. No.: 12/007,680

(22) Filed: Jan. 14, 2008

(65) Prior Publication Data
US 2008/0172196 A1  Jul. 17, 2008

(30) Foreign Application Priority Data
Jan. 16, 2007 (KR) .................. 10-2007-0004688

(51) Int. Cl.
*G06K 9/00* (2006.01)
(52) U.S. Cl. ........ 382/145; 382/141; 382/144; 382/149; 356/237.1; 356/137.2
(58) Field of Classification Search .......... 382/145, 382/149, 141, 144, 181; 356/237.2, 237.1
See application file for complete search history.

(56) References Cited

U.S. PATENT DOCUMENTS
| | | | |
|---|---|---|---|
| 2006/0068571 A1 | 3/2006 | Chow et al. | |
| 2006/0082766 A1* | 4/2006 | Kim et al. | 356/237.2 |
| 2008/0063258 A1* | 3/2008 | Kimba | 382/149 |

FOREIGN PATENT DOCUMENTS
| | | |
|---|---|---|
| JP | 2004-128197 | 4/2004 |
| JP | 2006-098163 | 4/2006 |
| KR | 1020040033525 | 4/2004 |
| KR | 1020060051443 | 5/2006 |

OTHER PUBLICATIONS

Saito, JP2004-128197, the english version translated by machine.*

* cited by examiner

*Primary Examiner* — Samir Ahmed
*Assistant Examiner* — Ruiping Li
(74) *Attorney, Agent, or Firm* — Harness, Dickey & Pierce, P.L.C.

(57) ABSTRACT

An inspection apparatus and a method for detecting defects in a substrate having a semiconductor device thereon are provided. The method includes establishing a first inspection region including first patterns repeatedly formed in a first direction and a second inspection region including second patterns repeatedly formed in a second direction on the substrate, determining a first unit inspection size of the first inspection region and a second unit inspection size of the second inspection region, obtaining images of the first and second patterns by moving the substrate in the first direction, and detecting defects in the first and second inspection regions by comparing the obtained images of portions of the first and second inspection regions, respectively, with each other. The first inspection size and second inspection size function as comparison units if defects are detected. The substrate may face an image receiving member.

14 Claims, 4 Drawing Sheets

SECOND DIRECTION

FIRST DIRECTION

METHOD FOR DETECTING DEFECTS IN A SUBSTRATE HAVING A SEMICONDUCTOR DEVICE THEREON

PRIORITY STATEMENT

This application claims the benefit of priority under 35 U.S.C. §119 to Korean Patent Application No. 2007-4688, filed on Jan. 16, 2007 in the Korean Intellectual Property Office (KIPO), the contents of which are incorporated herein by reference in their entirety.

BACKGROUND

1. Field

Example embodiments relate to a method for detecting defects in a substrate having a semiconductor device thereon. Other example embodiments relate to a method for detecting defects in a substrate having a semiconductor device thereon using a less complex process within a shorter amount of time.

2. Description of the Related Art

As processes for manufacturing a semiconductor device become more complex and critical dimensions of semiconductor devices decrease, problems may occur such as defects (e.g., bridges) between semiconductor patterns, breaking of the semiconductor patterns, voids in the semiconductor patterns, etc.

A process for detecting defects generated during processes for manufacturing a semiconductor device may be performed after performing each unit process thereof. If the detection process is accurately performed, successive processes may be performed without defects, preventing a decrease in a yield rate.

Comparison algorithms for detecting defects in a semiconductor device may be classified as a random mode algorithm or an array mode algorithm.

A random mode uses a die-to-die method in which a target die to be inspected is compared to an adjacent die. In the random mode, a first region of the target die may be compared to a second region of the adjacent die, which corresponds to the first region. If pixels in the first region are found to be different from those in the second region, defects may be present. In the random mode, corresponding regions between adjacent dies are compared with each other in order to detect defects in a region having irregular patterns therein and defects in a region having regular or repeated patterns therein. If defects are detected in the random mode, noise may increase due to a color difference or a focus difference between the adjacent dies. As the noise increases, detection power decreases.

In an array mode, images of repeated patterns on a die may be compared to one another at a predetermined interval. If a difference is found in the images of the repeated patterns, defects may be present. That is, a pixel having the different images may have defects. In the array mode, adjacent patterns on a die are compared to one another in order to detect defects in a region having the repeated patterns therein.

There are seldom color differences or focus differences between the adjacent patterns such that defects may be detected in the array mode more accurately than the random mode because adjacent regions, in which the repeated patterns are formed in one die, are compared to one another in the array mode. The signal-to-noise ratio (SNR) of the array mode may be about 1.5 times higher than that of the random mode. Minute defects may be accurately detected in the array mode due to the higher SNR thereof. Defects in a substrate having a highly-integrated semiconductor device thereon are usually detected using the array mode because the detection power of the array mode is higher than that of the random mode.

A semiconductor device may include a first region where patterns are repeatedly formed along an x-axis direction and a second region where patterns are repeatedly formed along a y-axis direction. The first and second regions, in which repetitive patterns are formed in different directions from each other, are inspected.

A substrate having a semiconductor device thereon is scanned in the x-axis direction with an image sensor so that images are obtained of first repetitive patterns in a first region, in which the first repetitive patterns are formed in the x-axis direction. The obtained images of the first repetitive patterns are compared to one another at predetermined intervals so that defects in the first region may be detected. After rotating the substrate by about 90 degrees in the same plane, the substrate is scanned in the y-axis direction with the image sensor so that images are obtained of second repetitive patterns in a second region, in which the second repetitive patterns are formed in the y-axis direction. The obtained images of the second repetitive patterns are compared to one another at predetermined intervals so that defects in the second region may be detected.

A time delay integration (TDI) sensor chip used in the array mode may be arranged in such a way that images of patterns may be obtained only in a scanning direction. As such, defects may be detected in a region where the patterns are repeatedly formed in the scanning direction. An inspection time may be longer if defects of the substrate are detected using the array mode, in which patterns are repeatedly formed on the substrate in the x-axis and y-axis directions, because the substrate is scanned in each of the x-axis and y-axis directions in order to detect the defects.

A peripheral portion of the region, in which the repetitive patterns are formed, may have a shape different from that of another portion of the region. As such, detecting defects in the peripheral portion of the region may be difficult using the array mode, in which images of the repetitive patterns in one portion of the region are compared to those of another portion of the region.

SUMMARY

Example embodiments relate to a method for detecting defects in a substrate having a semiconductor device thereon. Other example embodiments relate to a method for detecting defects in a substrate having a semiconductor device thereon using a less complex process within a shorter amount of time.

According to example embodiments, there is provided a method of detecting defects in a substrate having a semiconductor device. A first inspection region, in which first patterns are repeatedly formed in a first direction, and a second inspection region, in which second patterns are repeatedly formed in a second direction, may be established (or determined) in the substrate. A first unit inspection size of the first inspection region may be established (or determined). The first inspection size functions as a first comparison unit if defects are detected. A second unit inspection size of the second inspection region may be established (or determined). The second inspection size functions as a second comparison unit if defects are detected. Images of the first and second patterns in the first and second inspection regions, respectively, may be obtained by moving the substrate in the first direction. The substrate faces an image receiving member. Defects in the first inspection region may be detected by comparing the images in portions of the first inspection region with each other, wherein each of the portions has the first unit inspection size. Defects in the second inspection region may be detected by comparing the images in portions of the second inspection region with each other, wherein each of the portions has the second unit inspection size.

According to example embodiments, a first image in a first portion of the first inspection region may be obtained. Second and third images in second and third portions of the first inspection region may be obtained. Each of the first, second and third portions may have the first unit inspection size. The second and third portions may be adjacent to the first portions in the first direction. Gray levels of the first, second and third images may be compared by observing the difference in the pixels. A first difference between the gray level of the first image and the gray level of the second image may be calculated. A second difference between the gray level of the first image and the gray level of the third image may be calculated. It may be determined that a first position of the first portion has defects if the first and second differences of a pixel of the first image (corresponding to the first position) are over a predetermined value.

According to example embodiments, the first inspection region may include a portion of a cell region and a sense amplifier (SA) region of the semiconductor device. According to example embodiments, a central portion of the cell region may be set as the first inspection region and a peripheral portion of the cell region may be set as the second inspection region.

According to example embodiments, for detecting the defects in the second inspection region, a fourth image in a fourth portion of the second inspection region may be obtained. Fifth and sixth images in fifth and sixth portions of the second inspection region may be obtained. Each of the fourth, fifth and sixth portions may have the second unit inspection size. The fifth and sixth portions may be adjacent to the fourth portions in the second direction. Gray levels of the fourth, fifth and sixth images may be ascertained by comparing the pixels. A third difference between the gray level of the fourth image and the gray level of the fifth image and a fourth difference between the gray level of the fourth image and the gray level of the sixth image may be calculated. It may be determined that a second position of the fourth portion has a defect if the third and fourth differences of a pixel in the fourth image (corresponding to the second position) are over a predetermined value.

According to example embodiments, the second inspection region may include a split word line driver (SWD) region of the semiconductor device.

In some example embodiments, the method may include setting a region in which patterns are irregularly formed as a non-inspection region in the substrate.

According to example embodiments, obtaining the images in the first and second inspection regions may include obtaining images of patterns in portions of the first and second inspection regions along a first line by moving the substrate in the first direction until an edge of the substrate faces an image receiving member. Each of the portions may have a predetermined width. Each of the portions may obtain images of patterns in portions of the first and second inspection regions along a second line by moving the substrate in the first direction until an edge of the substrate faces the image receiving member. The second line may be adjacent to the first line.

According to example embodiments, the defects of the first inspection region may be immediately detected using the images obtained while the substrate is moving in the first direction.

According to example embodiments, the defects in the second inspection region may be detected after obtaining images of patterns in the portions of the first and second inspection regions, wherein a sum of the portions have the second unit inspection size.

According to example embodiments, the method may include collecting and synthesizing defects in the first and second inspection regions to indicate defect positions in the first and second inspection regions of the substrate, respectively.

According to other example embodiments, the second direction may be substantially perpendicular to the first direction.

According to example embodiments, an inspection process performed on a substrate, in which defects of the substrate are detected, by scanning the substrate only in one direction. Defects in a peripheral portion of a cell block may be detected using an array mode. As such, the defects in the substrate may be detected with accuracy within a decreased amount of time.

BRIEF DESCRIPTION OF THE DRAWINGS

Example embodiments will be more clearly understood from the following detailed description taken in conjunction with the accompanying drawings. FIGS. 1-5 represent non-limiting, example embodiments as described herein.

DETAILED DESCRIPTION OF EXAMPLE EMBODIMENTS

Various example embodiments will now be described more fully with reference to the accompanying drawings in which some example embodiments are shown. In the drawings, the thicknesses of layers and regions may be exaggerated for clarity.

Detailed illustrative embodiments are disclosed herein. However, specific structural and functional details disclosed herein are merely representative for purposes of describing example embodiments. This invention may, however, may be embodied in many alternate forms and should not be construed as limited to only example embodiments set forth herein.

Accordingly, while example embodiments are capable of various modifications and alternative forms, embodiments thereof are shown by way of example in the drawings and will herein be described in detail. It should be understood, however, that there is no intent to limit example embodiments to the particular forms disclosed, but on the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments. As used herein, the term "and/or" includes any and all combinations of one or more of the associated listed items.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the scope of example embodiments.

Spatially relative terms, such as "beneath," "below," "lower," "above," "upper" and the like, may be used herein for ease of description to describe one element or a relationship between a feature and another element or feature as illustrated in the figures. It will be understood that the spatially relative terms are intended to encompass different orientations of the device in use or operation in addition to the orientation depicted in the Figures. For example, if the device in the figures is turned over, elements described as "below" or "beneath" other elements or features would then be oriented "above" the other elements or features. Thus, for example, the term "below" can encompass both an orientation which is above as well as below. The device may be otherwise oriented (rotated 90 degrees or viewed or referenced at other orientations) and the spatially relative descriptors used herein should be interpreted accordingly.

Example embodiments are described herein with reference to cross-sectional illustrations that are schematic illustrations of idealized embodiments (and intermediate structures). As such, variations from the shapes of the illustrations as a result, for example, of manufacturing techniques and/or tolerances, may be expected. Thus, example embodiments should not be construed as limited to the particular shapes of regions illustrated herein but may include deviations in shapes that result, for example, from manufacturing. For example, an implanted region illustrated as a rectangle may have rounded or curved features and/or a gradient (e.g., of implant concentration) at its edges rather than an abrupt change from an implanted region to a non-implanted region. Likewise, a buried region formed by implantation may result in some implantation in the region between the buried region and the surface through which the implantation may take place. Thus, the regions illustrated in the figures are schematic in nature and their shapes do not necessarily illustrate the actual shape of a region of a device and do not limit the scope.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Unless otherwise defined, all terms (including technical and scientific terms) used herein have the same meaning as commonly understood by one of ordinary skill in the art to which example embodiments belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

In order to more specifically describe example embodiments, various aspects will be described in detail with reference to the attached drawings. However, the present invention is not limited to example embodiments described.

Example embodiments relate to an inspection device and a method for detecting defects in a substrate having a semiconductor device thereon. Other example embodiments relate to an inspection device and a method for detecting defects in a substrate having a semiconductor device thereon using a less complex process within a shorter amount of time.

Figure 1:
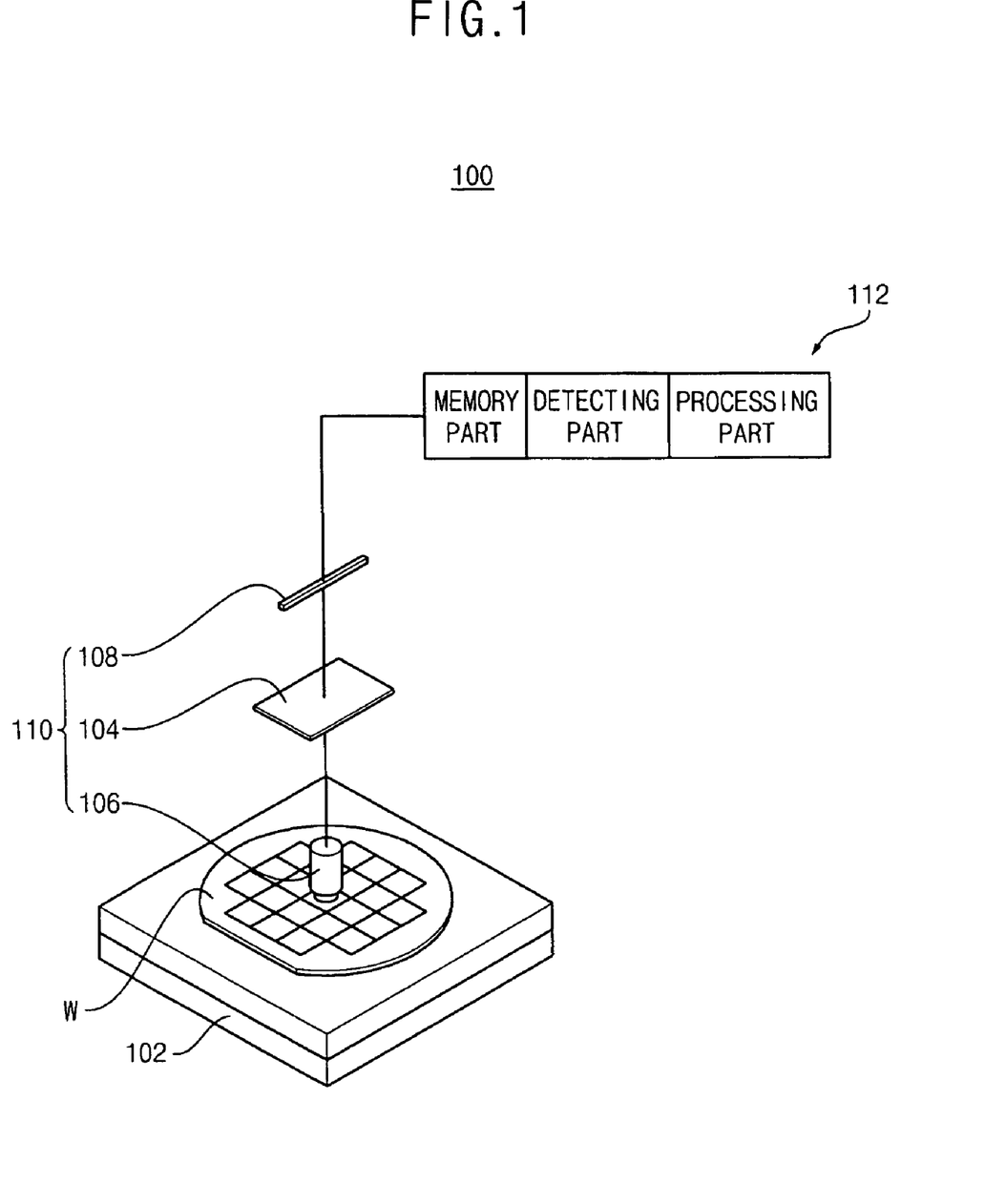
FIG. 1 is a diagram illustrating a perspective view of an inspection apparatus for detecting defects in a substrate in accordance with example embodiments.

FIG. 1 is a diagram illustrating a perspective view of an inspection apparatus for detecting defects in a substrate in accordance with example embodiments.

Referring to FIG. 1, an inspection apparatus 100 includes a stage 102, an imaging unit 110 and a defect detection unit 112.

A substrate W including a plurality of patterns for forming a semiconductor device may be mounted on the stage 102. A driving part (not shown) for moving the stage 102 may be connected to the stage 102. The stage 102 may be moved forward/backward and left/right and rotated by the driving part.

The imaging unit 110 takes pictures of the substrate W on the stage 102 and obtains images showing gradations in the substrate W. The defect detection unit 112 detects defects from the obtained images of the substrate W.

The imaging unit 110 may include a light source 104, an optical system 106 and an image sensor 108.

The light source 104 generates light and emits the light. The optical system 106 guides the light emitted from the light source 104 onto the substrate W. The optical system 106 receives light reflected from the substrate W and incident thereon. The image sensor 108 converts an image of the substrate W formed by the incident light of the optical system 106 into an electrical signal. The image sensor 108 outputs image data of patterns observed on the substrate W. Time delay integration (TDI) sensor chips (not shown) may be fixedly disposed (or formed) at the image sensor 108. Images of the patterns of a semiconductor device on the substrate W may be obtained from the image sensor 108 by moving the substrate W in a direction in which the TDI sensor chips are arranged.

The defect detection unit 112 may include a memory part, a detecting part and/or a processing part. The memory part may include an inspection region memory, an inspection size memory and an image data memory. The inspection region memory may establish and store an inspection region of a semiconductor device. The inspection size memory may store the unit size of a portion of the inspection region, wherein one portion of the inspection region having the unit size may be compared to another portion of the inspection region having the same size. The image data memory may store images obtained from the inspection region.

The detecting part may detect defects by comparing the obtained images to one another. The processing part may include a microcomputer having a central processing unit (CPU), which performs various kinds of operations (e.g., calculations), a memory device storing various kinds of information, etc.

A plurality of inspection regions (which vary according to a direction in which patterns are repeatedly formed) may be established and stored in the inspection region memory. For example, a region where patterns are repeatedly formed in a first direction may be established as a first inspection region and a region where patterns are repeatedly formed in a second direction may be established as a second inspection region.

The inspection size memory may store the size of each of the inspection regions or portions thereof, wherein each of the repetitive patterns is formed in a portion of the inspection region having the same size. The stored size may be referred to as a unit inspection size.

If the detecting part detects defects, the portions of a region of a semiconductor device having the unit inspection size are compared to one another. A specific portion of the region that is different from other portions may be considered to have defects. Portions of the region that are compared to others may be reduced as the unit inspection size becomes larger such that the inspection process may be performed in a shorter amount of time than the conventional art.

The image data memory may store images obtained from the inspection regions. Images obtained from different inspection regions may be stored in different storage regions.

The detecting part compares a first image of a first portion of an inspection region having the unit inspection size with second and third images of second and third portions of the inspection region, respectively, having the unit inspection size and being adjacent to the first portion.

The processing part calculates a difference between the gray level of the first image and the gray level of the second image. The processing part calculates a difference between the gray level of the first image and the gray level of the third image. The processing part may consider a pixel, which corresponds to an image having a difference in gray levels over a predetermined value, to have defects.

Hereinafter, a method of detecting defects in a substrate in accordance with example embodiments will be described with reference to FIGS. 1 to 5.

Figure 2:
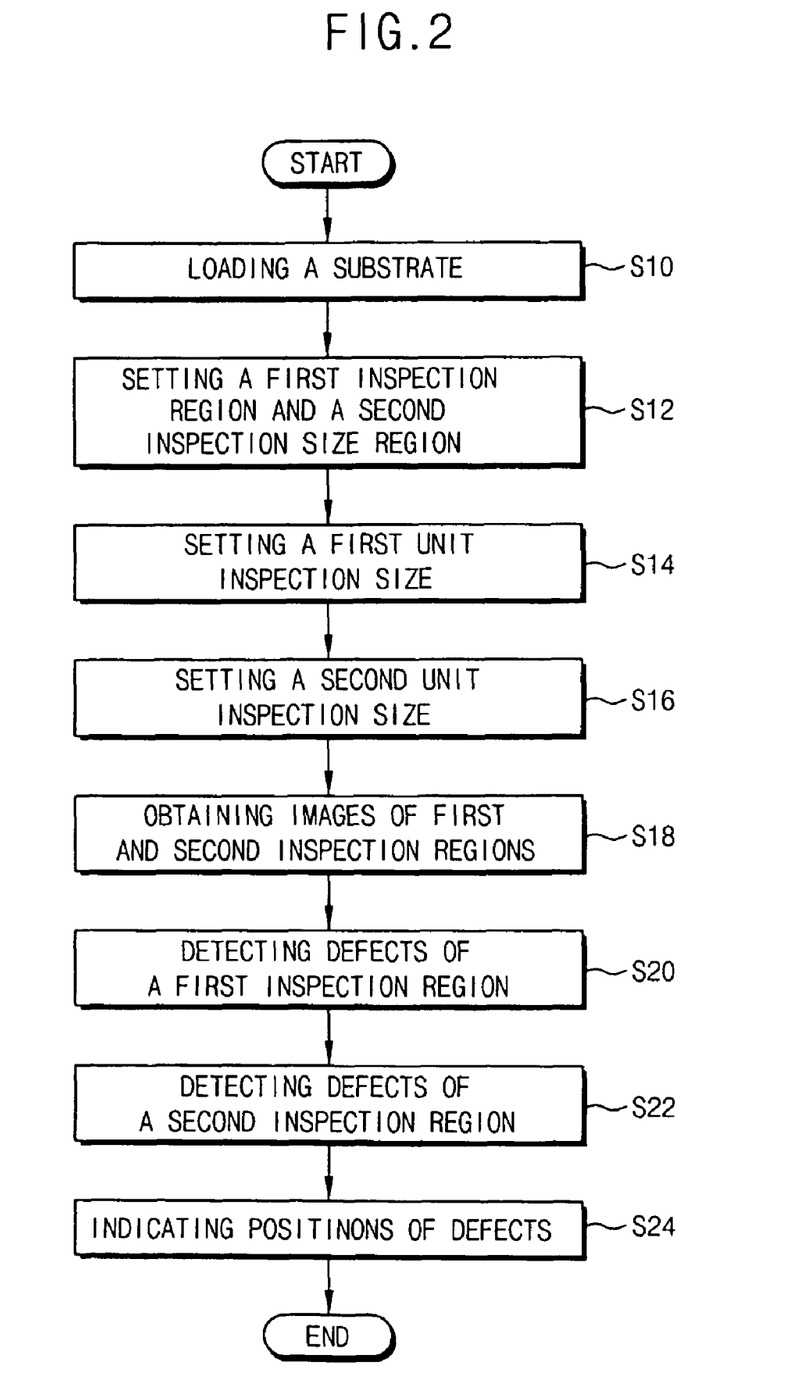
FIG. 2 is a flowchart illustrating a method of detecting defects in a substrate in accordance with example embodiments.

FIG. 2 is a flowchart illustrating a method of detecting defects in a substrate in accordance with example embodiments.

In step S10, a substrate having patterns thereon may be loaded on a stage 102. The patterns may form a memory device (e.g., a dynamic random access memory (DRAM) device, a flash memory device or the like). An imaging unit for obtaining images of the substrate may be disposed (or formed) over the substrate.

The memory device formed on the substrate may include a cell region including a plurality of unit cells and a peripheral region enclosing the cell region in which peripheral circuits are formed. A column decoder and a row decoder may be formed in a core region formed between the cell regions.

Figure 3:
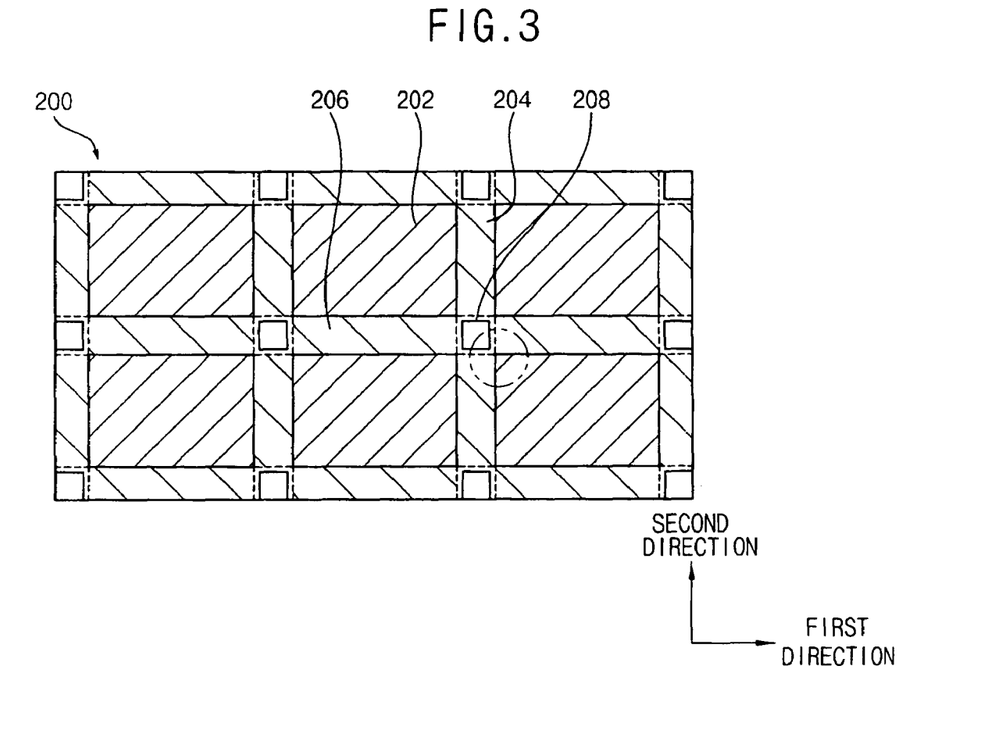
FIG. 3 is a diagram illustrating a plan view of a portion of a cell region of a memory device in accordance with example embodiments.
Figure 4:
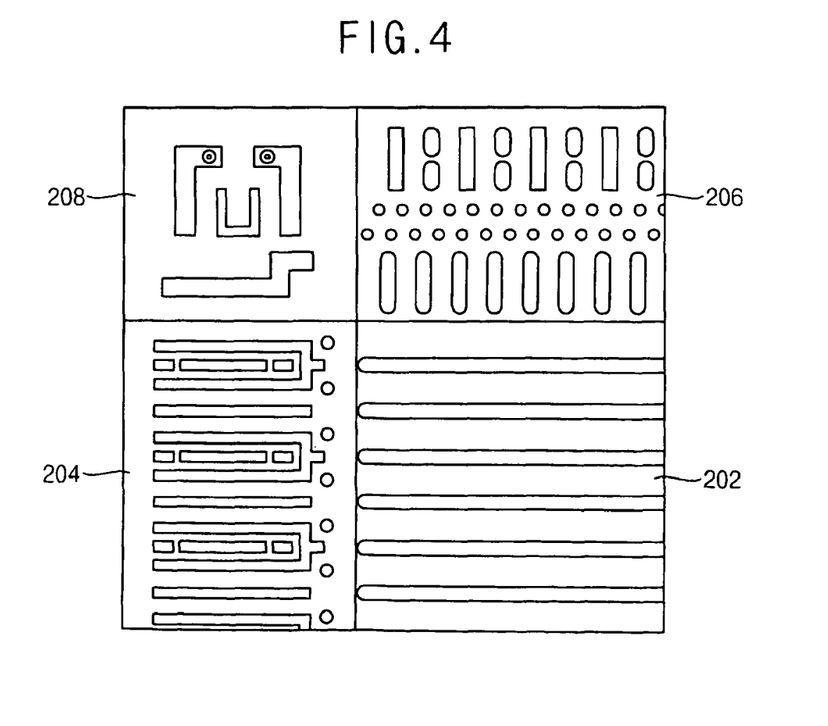
FIG. 4 is a diagram illustrating an enlarged plan view of an edge portion of a cell block of the cell region in FIG. 3.

FIG. 3 is a diagram illustrating a plan view of a portion of a cell region of a memory device. FIG. 4 is a diagram illustrating an enlarged plan view of an edge portion of a cell block of the cell region in FIG. 3.

Referring to FIGS. 3 and 4, a plurality of cell blocks 202 may be formed in a cell region 200. A split word line driver (SWD) region 204, a sense amplifier (SA) region 206 and a connection region 208 may be formed between the cell blocks 202. The SWD region 204 may be formed between the cell blocks 202 formed in a first direction. The SA region 206 may be formed between the cell blocks formed in a second direction substantially perpendicular to the first direction. The connection region 208 may be formed at a portion of the cell region in which the SWD region 204 and the SA region 206 intersect with each other.

Figure 5:
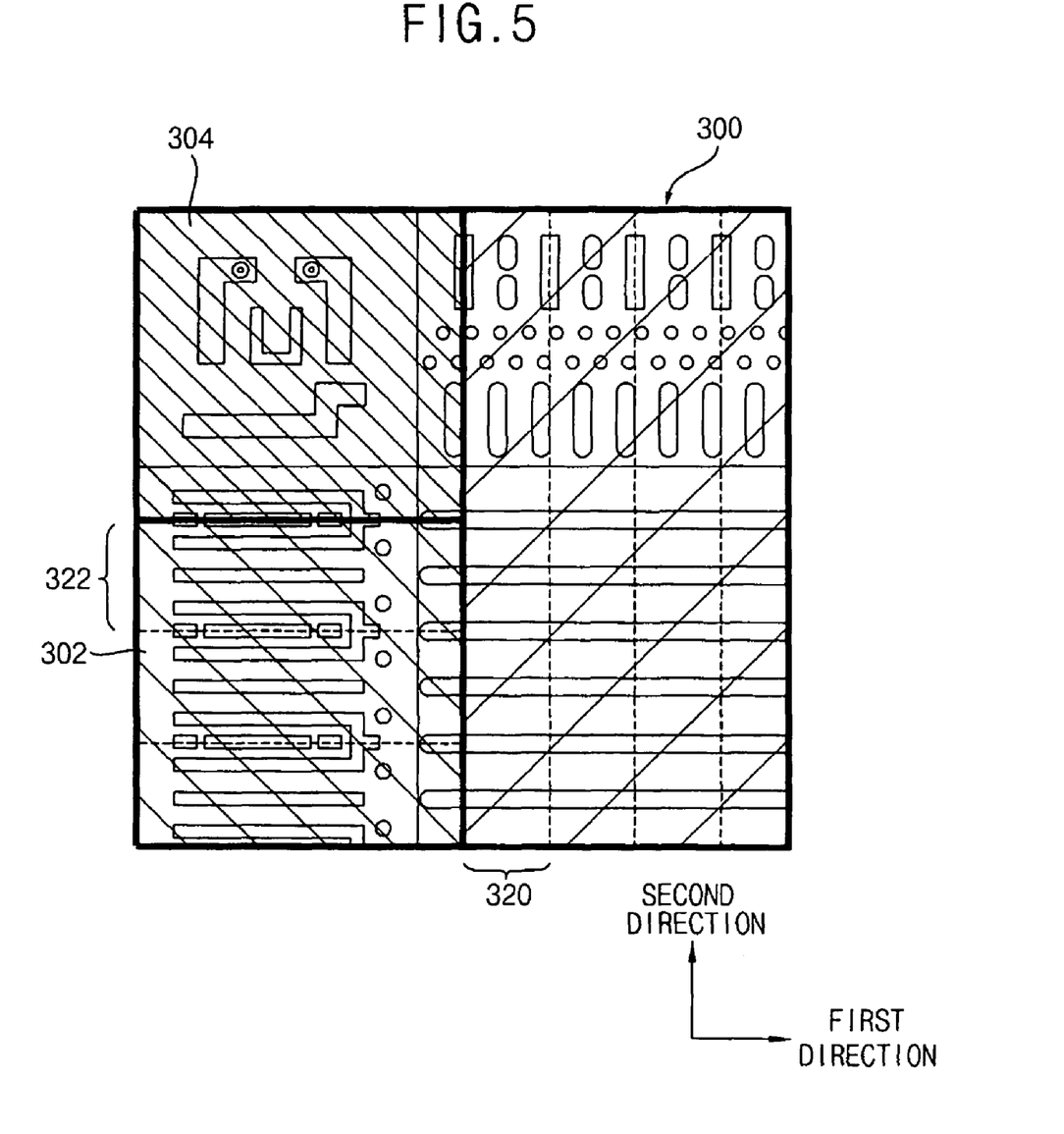
FIG. 5 is a diagram illustrating an enlarged plan view of a first inspection region and a second inspection region of the memory device in FIG. 3.

FIG. 5 is a diagram illustrating an enlarged plan view of a first inspection region and a second inspection region of the memory device in FIG. 3.

Referring to FIGS. 2 and 5, in step 12, a first inspection region 300 where first patterns are repeatedly formed in the first direction and a second inspection region 302 where second patterns are repeatedly formed in the second direction in the memory device on the substrate W may be established in the inspection region memory. The first and second directions may be substantially perpendicular to each other.

According to example embodiments, the first inspection region 300, in which a plurality of patterns is repeatedly formed in the first direction, may have a portion of the cell block 202 excluding a peripheral portion of the cell block 202 and the SA region 206. The second inspection region, in which a plurality of patterns is repeatedly formed in the second direction, may include the peripheral portion of the cell block 202 and the SWD region 204. The first and second inspection regions 300 and 302 may be set to include a plurality of regions having different sizes.

The first inspection region 300 may not include the peripheral portion of the cell block 202. As such, the first inspection region 300 may have a size smaller than that of the cell block region 202.

According to example embodiments, an edge of the first inspection region 300 may be distant from an edge of the cell block 202. The edge of the first inspection region 300 may be about 0.3 μm to about 1 μm from the edge of the cell block 202. If another cell block is not formed near the edge of the cell block 202, repetitive patterns are not formed near the edge of the cell block 202. As such, defects may not be detected in the peripheral portion of the cell block 202 using an array mode.

If patterns are repeatedly formed in the peripheral portion of the cell block 202 in the second direction, defects in the peripheral portion of the cell block 202 may be detected because the second inspection region 302 includes the peripheral portion of the cell block 202.

A non-inspection region 304 may include a portion of the cell region, in which repetitive patterns are not regularly formed. An inspection process may not be performed on the non-inspection region 304. The non-inspection region 304 may include the connection region 208, in which connection patterns for connecting peripheral circuits to each other are formed.

In step S14, a first unit inspection size 320 of the first inspection region 300 functioning as a comparison unit in an inspection process may be established. Patterns, included in one portion of the first inspection region 300, having the first unit inspection size 320 may have substantially the same shape as that of other patterns included in another portion of the first inspection region 300 having the first unit inspection size 320.

The first inspection region 300 may include different sub-regions of the memory device. The first unit inspection sizes 320 of the sub-regions may be different from each other.

In step S16, a second unit inspection size 322 of the second inspection region 302 functioning as a comparison unit in an inspection process may be established. Patterns, included in one portion of the second inspection region 302, having the second unit inspection size 322 may have substantially the same shape as that of other patterns included in another portion of the second inspection region 302 having the second unit inspection size 322.

The second inspection region 302 may include different sub-regions of the memory device. The second unit inspection sizes 322 of the sub-regions may be different from each other.

In step S18, images of patterns in the first and second inspection regions 300 and 302 may be obtained by moving the substrate W in the first direction with an image receiving member facing the substrate W. Images of the substrate W may be formed by the optical system 106. The images may be converted into electrical signals by the image sensor 108 so that image information may be obtained. The image information may be continuously generated by moving the stage 102 on which the substrate W is mounted in the first direction with the stage 102 facing the optical system 106.

The stage 102 moves along the first direction (e.g., from left to right) until an edge of the substrate W faces (or is aligned with) the optical system 106. Images of the patterns having a predetermined width on the substrate W may be obtained along a first line. The stage 102 moves in the opposite direction along the first direction (e.g., from right to left) until an edge of the substrate W faces (or is aligned with) the optical system 106. Images of patterns having the predetermined width on the substrate W may be obtained along a second line adjacent (or parallel) to the first line. If the stage 102 moves along the second line, the stage 102 moves in the opposite direction along the first direction (e.g. the opposite direction to that in which the stage 102 moves along the first line). As such, scanning the substrate W along the first and second lines may be performed in opposite directions. For example, if the substrate W is scanned from left to right to obtain images of the substrate W along the first line, the substrate W may be scanned from right to left to obtain images of the substrate W along the second line. Image information of the whole substrate W may be obtained by moving the stage 102 in the first direction (and in the reverse direction to the first direction) and obtaining images. Images of the patterns in the first and second inspection regions 300 and 302 may be each stored in the image data memory.

In step S20, images of patterns in a portion of the first inspection region 300 having the first unit inspection size 320 may be compared to images of other portions of the first inspection region 300 having the first unit inspection size 320 in order to detect defects in the first inspection region 300.

A first image may be obtained of first patterns in a first portion of the first inspection region 300 having the first unit inspection size 320. Second and third images may be obtained of second and third patterns in second and third portions of the first inspection region 300, respectively. The second and third portions may be adjacent to the first portion and have the first unit inspection size 320. The first, second and third patterns may be substantially the same. As such, the first second and third images may have substantially the same shape if defects do not exist in the first, second or third portions of the first inspection region 300. The gray level of the first image may be compared by the pixels to the gray levels of the second and third images, respectively. A difference between the gray level of the first image and that the gray level of the second image, and a difference between the gray level of the first image and that the gray level of the third image may be calculated (or ascertained), respectively. A pixel of the first image having a difference in gray levels over a predetermined (or threshold) value may be considered to have defects.

For example, if defects exist in the first portion of the first inspection region 300 (that corresponds to the first image) and do not exist in the second or third portions of the first inspection region 300 (that correspond to the second and third images, respectively) then a first gray level difference between the first and second images and a second gray level difference between the first and third images may be substantially large. As such, if both of the first and second gray level differences are over a predetermined (or threshold) value, then the first portion of the first inspection region 300 may have defects.

Repetitive patterns may be formed in the first inspection region 300 in a direction substantially the same as that in which the substrate W moves (i.e., the first direction) if images of the patterns are obtained in a previous process. After obtaining images when the substrate W is moving, defects in the first inspection region 300 may be immediately detected using the obtained images. As such, defects in the first inspection region 300 may be detected in real time while the substrate W is moving.

In step S22, images of patterns in a portion of the second inspection region 302 having the second unit inspection size 322 may be compared to those of other portions of the second inspection region 302 having the second unit inspection size 322 in order to detect defects in the second inspection region 302.

A fourth image may be obtained of fourth patterns in a fourth portion of the second inspection region 302 having the second unit inspection size 322. Fifth and sixth images may be obtained of fifth and sixth patterns in fifth and sixth portions of the second inspection region 302, respectively. The fifth and sixth portions may be adjacent to the fourth portion and have the second unit inspection size 322. The fourth, fifth and sixth patterns may be substantially the same. As such, the fourth, fifth and sixth images may have substantially the same shape if defects do not exist in the fourth, fifth and sixth portions of the second inspection region 302.

The gray level of the fourth image may be compared by pixel to each of the gray levels of the fifth and sixth images. A difference between the gray level of the fourth image and the gray level of the fifth image may be calculated (or ascertained). A difference between the gray level of the fourth image and the gray level of the sixth image may be calculated (or ascertained). A pixel of the fourth image, having a difference in the gray levels over a predetermined value, may have defects.

For example, if defects exist in the fourth portion of the second inspection region 302 corresponding to the fourth image and do not exist in the fifth and sixth portions of the second inspection region 302 corresponding to the fifth and sixth images, a third gray level difference between the fourth and fifth images and a fourth gray level difference between the fourth and sixth images may be large. As such, if both of the third and fourth gray level differences are over a predetermined value, the fourth portion of the second inspection region 302 may have defects.

Repetitive patterns may be formed in the second inspection region 302 in a direction substantially perpendicular to that in which the substrate W is moving (i.e., the second direction) if images of the patterns are obtained in a previous process. Even after obtaining images while the substrate W is moving, defects in the second inspection region 302 may not be immediately detected. After scanning the substrate W in the first direction several times, images of the patterns in portions of the second inspection region 302 may be obtained wherein the sum of the portions of the second inspection region 302 have the second inspection size 322. As such, the defects in the second inspection region 302 may be detected.

Images in the non-inspection region 304 where patterns of the memory device are irregularly formed may not be stored in the image data memory. Images in the non-inspection region 304, where patterns of the memory device are irregularly formed, may not be used for an inspection process.

In step S24, positions of the defects of the substrate W may be indicated (or identified) by combining the defects in the first and second inspection regions 300 and 302.

As illustrated above, defects of a substrate may be detected by scanning the substrate only in one direction. Defects in a peripheral portion of a cell block may be detected using an array mode.

According to example embodiments, an inspection process may be performed on a substrate in which defects of the substrate may be detected by scanning the substrate only in one direction such that the amount of time necessary for performing the inspection may be reduced.

Defects in a peripheral portion of a cell block may be detected using an array mode in order to detect the defects more accurately. As such, succeeding processes may be performed only if defects do not exist, increasing the yield rate of a semiconductor device.

The foregoing is illustrative of example embodiments and is not to be construed as limiting thereof. Although a few example embodiments have been described, those skilled in the art will readily appreciate that many modifications are possible in example embodiments without materially departing from the novel teachings and advantages. Accordingly, all such modifications are intended to be included within the scope of this invention as defined in the claims. In the claims, means-plus-function clauses are intended to cover the structures described herein as performing the recited function, and not only structural equivalents but also equivalent structures. Therefore, it is to be understood that the foregoing is illustrative of various example embodiments and is not to be construed as limited to the specific embodiments disclosed, and that modifications to the disclosed embodiments, as well as other embodiments, are intended to be included within the scope of the appended claims.

What is claimed is:

1. A method of detecting defects in a substrate, the method comprising:

establishing a first inspection region including at least one first pattern repeatedly formed in a first direction on the substrate, the first inspection region including a portion of a cell block, and a second inspection region including at least one second pattern repeatedly formed in a second direction on the substrate, the second inspection region including a peripheral portion of the cell block, wherein a semiconductor device is mounted on the substrate;

determining a first unit inspection size of the first inspection region, wherein the first unit inspection size functions as a first comparison unit if defects are detected;

determining a second unit inspection size of the second inspection region, wherein the second unit inspection size functions as a second comparison unit if defects are detected;

obtaining at least one image of the first pattern in the first inspection region and at least one image of the second pattern in the second inspection region by moving the substrate in the first direction, wherein the substrate faces an image receiving member;

detecting defects in the first inspection region by comparing portions of the images obtained from the first inspection region with each other, wherein each of the portions has the first unit inspection size; and detecting defects in the second inspection region by comparing portions of the images obtained from the second inspection region with each other, wherein each of the portions has the second unit inspection size.

2. The method of claim 1, wherein detecting defects in the first inspection region includes:

obtaining a first image of a first portion of the first inspection region, a second image of a second portion of the first inspection region and a third image of a third portion of the first inspection region, each of the first, second and third portions having the first unit inspection size, wherein the second and third portions are adjacent to the first portion in the first direction;

comparing gray levels of the first, second and third images by each pixel;

ascertaining a first difference between the gray level of the first image and the gray level of the second image;

ascertaining a second difference between the gray level of the first image and the gray level of the third image; and determining that the first portion has a defect if the first and second differences of a pixel in the first image are over a predetermined value.

3. The method of claim 2, wherein ascertaining the first and second differences includes calculating the first and second differences.

4. The method of claim 2, wherein detecting defects in the second inspection region includes:

obtaining a fourth image of a fourth portion of the second inspection region, a fifth image of a fifth portion of the second inspection region and a sixth image of a sixth portion of the second inspection region, each of the fourth, fifth and sixth portions having the second unit inspection size, wherein the fifth and sixth portions are adjacent to the fourth portion in the second direction;

comparing gray levels of the fourth, fifth and sixth images by each pixel;

ascertaining a third difference between the gray level of the fourth image and the gray of the fifth image; and ascertaining a fourth difference between the gray level of the fourth image and the gray level of the sixth image; and determining that the fourth portion has a defect if the third and fourth differences of a pixel in the fourth image are over a predetermined value.

5. The method of claim 4, wherein ascertaining the third and fourth differences includes calculating the third and fourth differences.

6. The method of claim 1, wherein the first inspection region includes a portion of a cell region and a sense amplifier (SA) region of the semiconductor device.

7. The method of claim 6, wherein a central portion of the cell region is established as the first inspection region and a peripheral portion of the cell region is established as the second inspection region.

8. The method of claim 1, wherein obtaining images of the first and second inspection regions includes:

obtaining images of a first portion of the first pattern in the first inspection region along a first line and images of a first portion of the second pattern in the second inspection region along the first line by moving the substrate in the first direction until an edge of the substrate is aligned with an image receiving member, wherein each of the first portion of the first and second patterns has a predetermined width; and obtaining images of a second portion of the first pattern in the first inspection region along a second line and images of a second portion of the second pattern in the second inspection region along the second line by moving the substrate in the first direction until an edge of the substrate is aligned with the image receiving member, wherein the second line is adjacent to the first line.

9. The method of claim 8, wherein the defects in the first inspection region are immediately detected using the images obtained while the substrate is moving in the first direction.

10. The method of claim 8, wherein the defects in the second inspection region are detected after obtaining the images of the first and second portions of the first pattern in the first inspection region and the images of the first and second portions of the second pattern in the second inspection region, wherein a sum of the first and second portions of the second pattern in the second inspection region is equal to the second unit inspection size.

11. The method of claim 1, wherein the second inspection region includes a split word line driver (SWD) region of the semiconductor device.

12. The method of claim 1, further comprising establishing a region in which patterns are irregularly formed as a non-inspection region in the substrate.

13. The method of claim 1, further comprising combining the defects detected in the first and second inspection regions such that defect positions in the first and second inspection regions of the substrate, respectively, are identified.

14. The method of claim 1, wherein the second direction is substantially perpendicular to the first direction.

* * * * *